(12) United States Patent
Matouq et al.

(10) Patent No.: US 11,852,616 B2
(45) Date of Patent: Dec. 26, 2023

(54) HIGH PRESSURE HIGH TEMPERATURE DIRECT FLUID INJECTION TO GAS CHROMATOGRAPHY IN A PVT SYSTEM

(71) Applicant: SAUDI ARABIAN OIL COMPANY, Dhahran (SA)

(72) Inventors: Hana Matouq, Dhahran (SA); Mohammed Sajjad Ali, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 210 days.

(21) Appl. No.: 17/143,618

(22) Filed: Jan. 7, 2021

(65) Prior Publication Data

US 2022/0214317 A1    Jul. 7, 2022

(51) Int. Cl.
*G01N 30/06* (2006.01)
*G01N 30/20* (2006.01)
*G01N 30/88* (2006.01)
*G01N 33/28* (2006.01)
*G01N 25/12* (2006.01)

(Continued)

(52) U.S. Cl.
CPC ............ *G01N 30/06* (2013.01); *G01N 25/12* (2013.01); *G01N 30/20* (2013.01); *G01N 30/88* (2013.01); *G01N 33/2823* (2013.01); *B01D 3/06* (2013.01); *E21B 49/088* (2013.01); *G01N 2030/025* (2013.01); *G01N 2030/065* (2013.01); *G01N 2030/201* (2013.01); *G01N 2030/522* (2013.01); *G01N 2030/8854* (2013.01)

(58) Field of Classification Search
CPC .. B01D 3/06; E21B 49/088; G01N 2030/025; G01N 2030/065; G01N 2030/201; G01N 2030/522; G01N 2030/8854; G01N 25/12; G01N 30/06; G01N 30/20; G01N 30/88; G01N 33/2823

See application file for complete search history.

(56) References Cited

U.S. PATENT DOCUMENTS 4,726,238 A   2/1988  Reese et al.
4,726,398 A * 2/1988  Barree .................. F16K 11/044
                                                137/625.5

(Continued)

FOREIGN PATENT DOCUMENTS

CN           1536359 A     10/2004
CN         102121891 A      7/2011

(Continued)

OTHER PUBLICATIONS

Gabitto et al, Final Progress Report Experimental and Theoretical Determination of Heavy Oil Viscosity Under Reservoir Conditions (Year: 2003).*

(Continued)

*Primary Examiner* — David L Singer
(74) *Attorney, Agent, or Firm* — Osha Bergman Watanabe & Burton LLP

(57) ABSTRACT

A system includes a phase behavior analysis unit having a housing, a heating system connected to the housing and arranged to heat an interior of the housing, a pressure cell positioned in the interior of the housing, and a three-way valve with one inlet fluidly connected to a chamber in the pressure cell and two outlets. The system also includes a gas chromatograph that is fluidly coupled to the chamber in the pressure cell via the three-way valve.

20 Claims, 4 Drawing Sheets

(51) Int. Cl.
*G01N 30/02* (2006.01)
*G01N 30/52* (2006.01)
*B01D 3/06* (2006.01)
*E21B 49/08* (2006.01)

(56) References Cited

U.S. PATENT DOCUMENTS

| | | | |
|---|---|---|---|
| 8,991,233 B2 | 3/2015 | Kriel et al. | |
| 2007/0187092 A1* | 8/2007 | Mullins | E21B 47/06 166/100 |
| 2009/0151426 A1* | 6/2009 | Shah | G01N 33/2823 73/23.35 |
| 2011/0185809 A1* | 8/2011 | Guieze | G01N 1/2202 73/23.35 |
| 2012/0011919 A1* | 1/2012 | Kriel | G01N 30/88 73/23.35 |
| 2012/0272715 A1* | 11/2012 | Kriel | G01N 33/241 73/23.42 |
| 2014/0123728 A1* | 5/2014 | Mostowfi | G01N 1/4022 210/103 |
| 2017/0002646 A1* | 1/2017 | Bonavides | E21B 47/107 |
| 2017/0146688 A1* | 5/2017 | Sugiyama | G01F 1/8409 |
| 2017/0175521 A1* | 6/2017 | Pirolli | E21B 49/082 |
| 2018/0031527 A1 | 2/2018 | Choi et al. | |

FOREIGN PATENT DOCUMENTS

| | | | | |
|---|---|---|---|---|
| CN | 102135484 B | | 2/2012 | |
| CN | 101887051 B | | 6/2012 | |
| CN | 103221819 A | * | 7/2013 | ............ G01N 30/88 |
| CN | 103454362 B | | 11/2014 | |
| CN | 206002471 U | * | 3/2017 | |
| CN | 105671385 B | * | 5/2017 | |
| CN | 105092419 B | | 9/2017 | |
| CN | 108225824 A | | 6/2018 | |
| WO | 2009079059 A1 | | 6/2009 | |

OTHER PUBLICATIONS

Chandler Engineering, Model 2353 Equilibrium Flash Separator (Year: 2008).*

Lansangan et al, Mercury-Free PVT Apparatus for Thermophysical Property Analyses of Hydrocarbon Reservoir Fluids, (Year: 1992).*

Rob Bohn, NEMA 4 & Nema 4X Enclosures—Class 1, Div 2 Enclosure Protection (Year: 2014).*

Luong, Jim et al., "Innovations in High-Pressure Liquid Injection Technique for Gas Chromatography: Pressurized Liquid Injection System", Journal of Chromatographic Science, vol. 41, Nov.-Dec. 2003, pp. 550-559 (10 pages).

Fraser, Murray, "Designing On-Line Chromatograph Systems for Liquid Fractionation Facilities", Daniel Measurement and Control, 1998, pp. 1-16 (16 pages).

International Search Report and Written Opinion of the International Searching Authority issued in corresponding International Application No. PCT/US2022/011579, dated Apr. 26, 2022 (12 pages).

Kriel, W.A. et al., "Improved Gas Chromatographic Analysis of Reservoir Gas and Condensate Samples"; Proceedings of the SPE International Symposium on Oilfield Chemistry; Paper No. SPE-25190-MS; pp. 1-15; Mar. 2, 1993 (15 pages).

* cited by examiner

HIGH PRESSURE HIGH TEMPERATURE DIRECT FLUID INJECTION TO GAS CHROMATOGRAPHY IN A PVT SYSTEM

BACKGROUND

Phase behavior analysis may be used in reservoir engineering to analyze the fluid properties of reservoir fluids (e.g., gas condensates and oil). Phase behavior analysis includes fluid analysis used in predicting the fluid's behavior under different pressures (P), volumes (V), and temperatures (T). Accordingly, phase behavior analysis may often be referred to as PVT analysis. Phase behavior (PVT) analysis may be used to analyze and predict the volumetric and phase behavior of the reservoir fluid as it travels from the reservoir into production pipelines, as well as the reservoir fluid remaining in the reservoir as the reservoir pressure decreases with production. For example, fluid composition, viscosity, density, and compressibility may change with pressure and temperature changes. As such, phase behavior (PVT) analysis may be used for designing and optimizing reservoir production, including reservoir fluid extraction and processing, as the fluid undergoes pressure and temperature changes from production. For example, PVT analysis may be used to set parameters for reservoir simulations, which may be used for planning enhanced oil recovery processes, for designing flow systems (flow assurance), and for other reservoir production processes. Fluid characterization from PVT analysis may include, for example, solids onset and deposition, P-T solubility boundaries, chemical incompatibilities, compositional exchanges from gas injection and production, and changes in fluid rheology (flow) behavior.

PVT analysis is often performed on representative fluid samples of a reservoir fluid as soon after the sample is collected as possible. For example, fluid samples are often collected while drilling a first exploration well into the reservoir, and before the reservoir is put into full production. Once a fluid sample is collected, it may be placed in an above ground PVT system (e.g., in a lab), where it may be tested at reservoir pressures and temperatures to determine phase behavior and compositional changes of the fluid through the life of the reservoir as pressure decreases.

In a typical PVT system, a fluid sample is separated into two parts, gas and liquid. Each part is then collected and transferred to a lab for analysis. In one type of analysis, the gas and liquid parts may be separately injected into a gas chromatograph in separate processes in order to find the molar composition of each part. However, during the fluid collection and transfer to the lab, some of the light components of the fluid sample may evaporate and escape, thereby affecting the sample composition, which may cause inaccurate results in the molar composition.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments of the present disclosure relate to systems that include a phase behavior analysis unit having a housing, a heating system connected to the housing and arranged to heat an interior of the housing, a pressure cell positioned in the interior of the housing, and a three-way valve with one inlet fluidly connected to a chamber in the pressure cell and two outlets, where a gas chromatograph may be fluidly coupled to the chamber in the pressure cell via the three-way valve.

In another aspect, embodiments of the present disclosure relate to methods that include conducting a phase behavior analysis on a fluid sample from a well in a phase behavior analysis unit, where the phase behavior analysis unit may have a pressure cell with a chamber containing the fluid sample, a three-way valve with an inlet fluidly connected to the chamber, and at least one measurement device, and transferring a portion of the fluid sample via the three-way valve to a gas chromatograph located outside of the phase behavior analysis unit.

In yet another aspect, embodiments of the present disclosure relate to methods of analyzing a fluid sample taken from a reservoir under a reservoir pressure and a reservoir temperature that includes using a computing system to control a phase behavior analysis of the fluid sample in a phase behavior analysis unit, the computing system located outside of the phase behavior analysis unit. Controlling the phase behavior analysis may include maintaining the reservoir temperature inside the phase behavior analysis unit during the phase behavior analysis and providing the reservoir pressure inside the phase behavior analysis unit. The methods may also include using the computing system to open a three-way valve within the phase behavior analysis unit and direct a portion of the fluid sample through the three-way valve under the reservoir temperature and the reservoir pressure and directing the portion of the fluid sample from the three-way valve to a gas chromatograph located outside of the phase behavior analysis unit.

Other aspects and advantages of the claimed subject matter will be apparent from the following description and the appended claims.

DETAILED DESCRIPTION

Figure 1:
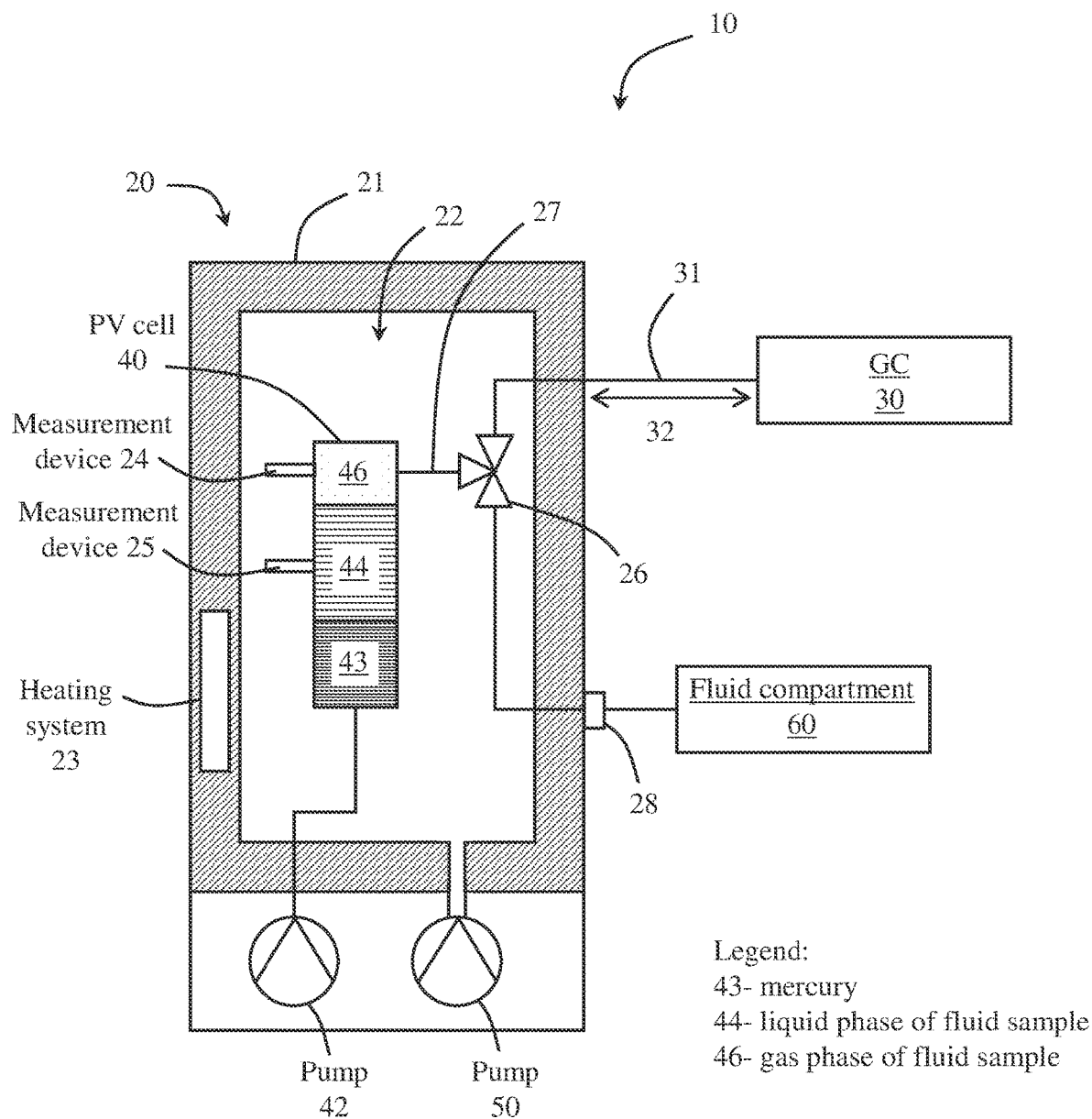
FIG. 1 shows a schematic view of a system according to embodiments of the present disclosure.

In one aspect, embodiments disclosed herein generally relate to analysis of a fluid sample from a reservoir using phase behavior analysis (which may be referred to herein as PVT analysis) and gas chromatography. PVT analysis may be conducted on reservoir fluid samples to simulate what takes place in the reservoir and/or at the surface during reservoir production. Accordingly, PVT analysis may be conducted, at least in part, under pressures and temperatures that mimic the pressures and temperatures in which the reservoir fluid is exposed to in the reservoir and/or during production. PVT analysis may include separating phases from a fluid sample and analysis of the fluid sample as it undergoes phase separation. For example, PVT analysis may include measuring properties of a fluid sample, such as phase behavior, density, viscosity, and compressibility, as gas evolves from oil when the pressure falls below the bubble point. Gas chromatography may be used to analyze the composition of the fluid sample, including analysis of one or more phases separated during the PVT analysis.

According to embodiments of the present disclosure, a gas chromatograph ("GC") may be connected, e.g., via one or more flow lines, to a phase behavior analysis unit (referred to herein as a PVT unit) such that at least a portion of a fluid sample may be directly injected through a flow line from the PVT unit to the GC under simulated reservoir conditions, which may be high temperature and high pressure conditions. For example, a portion of a fluid sample may be transferred directly between a PVT unit and a connected GC under a pressure ranging between 5,000 and 7,000 psi, such as about 6,000 psi, and a temperature ranging between 200° F. and 400° F., such as about 300° F. A portion of the fluid sample may be transferred to the connected GC either during or after undergoing PVT analysis in the PVT unit. Accordingly, the portion of the fluid sample transferred to the GC may be a separated portion of the fluid sample (e.g., at least part of a separated gas phase of the fluid sample or at least part of a separated liquid phase of the fluid sample) that was separated during the PVT analysis. By transferring a portion of the fluid sample to the GC directly from a PVT unit holding the fluid sample under simulated reservoir fluid pressure and temperature conditions, independent collection and transfer of the separated fluids outside of the PVT unit may be avoided. Direct transfer described herein may also aid in reducing the possibility of losing light components (e.g., light hydrocarbons such as methane and ethane) that can evaporate and escape from the fluid sample during the collection and transferring process.

The fluid connection between the GC to the PVT unit may include a three-way valve located inside the PVT unit, such that fluids being transferred through the three-way valve may be transported under the pressure and temperature conditions in the PVT unit (e.g., high pressure high temperature simulated reservoir conditions). The three-way valve may have an inlet fluidly connected to the fluid sample held in the PVT unit, a first outlet fluidly connected to an inlet to the GC (for injection and analysis of the separated fluids being transferred from the PVT unit to the GC), and a second outlet. The second outlet of the three-way valve may be fluidly connected to an exit port of the PVT unit, which may provide outside access to the fluid sample inside the PVT unit. For example, the second outlet of the three-way valve may be used to transfer and collect at least a portion of a fluid sample outside of the PVT unit for purposes other than gas chromatography. In this manner, fluid from the fluid sample may be directly injected to the connected GC through the first outlet or directly injected through the second outlet (e.g., to a second testing apparatus or fluid collection container) while also preserving as much as possible the pressure and temperature conditions from inside the PVT unit (e.g., simulated reservoir pressure and temperature conditions) and reducing the likelihood of losing light components from the fluid sample.

For example, FIG. 1 shows a system 10 including a PVT unit 20 and a connected GC 30 according to embodiments of the present disclosure. The PVT unit 20 may include a housing 21 defining an interior chamber 22 of the PVT unit 20. The housing 21 may be pressure sealed, such that one or more pressure cells (which may be referred to as "PV cells") 40, one or more measurement devices 24, 25, and a three-way valve 26 may be held in the interior 22 of the housing 21 under a pressurized environment. The interior 22 of the housing 21 may be pressurized, for example, using a pump 50 fluidly connected to the interior 22 of the housing 21 or other pressurizing systems. Additionally, a heating system 23 may be connected to the housing 21 and arranged to heat the interior 22 of the housing 21, and thus also heat the PV cell(s) 40, measurement devices 24, 25, and three-way valve 26. For example, the heating system 23 may include a plurality of heating coils extending through the housing wall or other known type of heating system.

The three-way valve 26 may include one inlet fluidly connected to a fluid sample chamber in the PV cell 40 and two outlets. The inlet of the three-way valve 26 may be fluidly connected to the PV cell 40 via a flow line 27 extending a distance between the PV cell 40 and the inlet of the three-way valve 26, or by mounting the three-way valve 26 directly to the PV cell 26, where the inlet of the three-way valve 26 is fluidly connected to the fluid sample chamber of the PV cell 40.

A first outlet of the three-way valve 26 may be fluidically coupled to the GC 30 via a flow line 31. In such arrangement, the GC 30 may be fluidly connected to the fluid sample chamber in the PV cell 40 via the flow line 31 and the three-way valve 26. The GC 30 may be provided adjacent to the PVT unit 20 or a distance 32 away from the PVT unit 20. The closer the GC 30 is to the PVT unit, the less distance the fluid sample needs to travel outside of the pressure and temperature conditions within the PVT unit 20. Accordingly, when the GC 30 is positioned as close as possible to the PVT unit 20, the likelihood of the fluid sample being altered during transmission may be reduced. For example, a connected GC 30 may be positioned a distance 32 less than 5 ft, less than 3 ft, or less than 2 ft.

A second outlet of the three-way valve 26 may be fluidly connected to an exit port 28 of the PVT unit 20. The exit port 28 may be formed in the wall of the housing 21 or may be located outside of the PVT unit. In such manner, a fluid connection between the outside of the PVT unit 20 and the fluid sample chamber within the PV cell 40 may be provided through the three-way valve 26. A fluid testing apparatus other than a GC or a fluid collection container may be connected to the exit port 28 to collect fluid from the PV cell 40 via the three-way valve 26. For example, in the embodiment shown, a fluid compartment 60 may be fluidly connected to the second outlet of the three-way valve 26 via the exit port 28, where the fluid compartment is positioned outside of the PVT unit 20.

According to embodiments of the present disclosure, a three-way valve 26 may be a ball valve made of a material capable of withstanding high pressure (e.g., at least 7,000 psi), high temperature (e.g., up to 400° C.), and corrosive environments, such as sour gas conditions (e.g., carbon dioxide ($CO_2$) and hydrogen sulfide ($H_2S$)). For example, a three-way valve 26 may be made of nickel-molybdenum alloys, such as Hastelloy alloys, including but not limited to nickel-chromium-molybdenum alloys, which may withstand high pressure, high temperature conditions and corrosive environments. Valve connections may likewise be made of a non-corrosive, high pressure high temperature material, such as nickel-molybdenum alloys.

The PV cell 40 may be removable or fixed in place. For example, in embodiments having a removable PV cell 40, the PV cell may be filled with a fluid sample outside of the PVT unit 20 and then positioned inside the PVT unit 20 for testing. In some embodiments having a PV cell fixed within the PVT unit, a fluid line may extend through the PVT unit housing to fluidly connect a fluid source located outside of the PVT unit to the fluid sample chamber within the fixed PV cell. In some embodiments having a PV cell fixed within the housing interior of the PVT unit, an access door to the PVT unit housing may be opened to access the fixed PV cell and inject a fluid sample into the fixed PV cell. Further, one PV cell 40 is shown in the system 10 of FIG. 1, but other embodiments of a PVT unit may include more than one PV cell.

According to embodiments of the present disclosure, a PV cell 40 may be pressurized by the pressurizing system (e.g., pump 50) of the PVT unit housing and/or the PV cell 40 may be individually pressurized. When the pressure within the fluid sample chamber in the PV cell 40 is changed (reduced or increased), a fluid sample inside the fluid sample chamber may separate into a gas phase 46 and a liquid phase 44. For example, in the system 10 shown in FIG. 1, a pump 42 may be configured to pressurize a fluid sample 44, 46 in the PV cell 40 by pumping mercury 43 into and out of the fluid sample chamber of the PV cell 40. In other embodiments, different pressurizing systems may be used to charge a fluid sample in the PV cell. Further, different configurations of one or more PV cells, measuring devices, and exteriorly connected equipment (e.g., a GC, a fluid collection container, or other testing equipment) may be used while maintaining a more efficient transfer of a fluid from the PV cell to the exteriorly connected equipment using a three-way valve positioned within the PVT unit.

Figure 2:
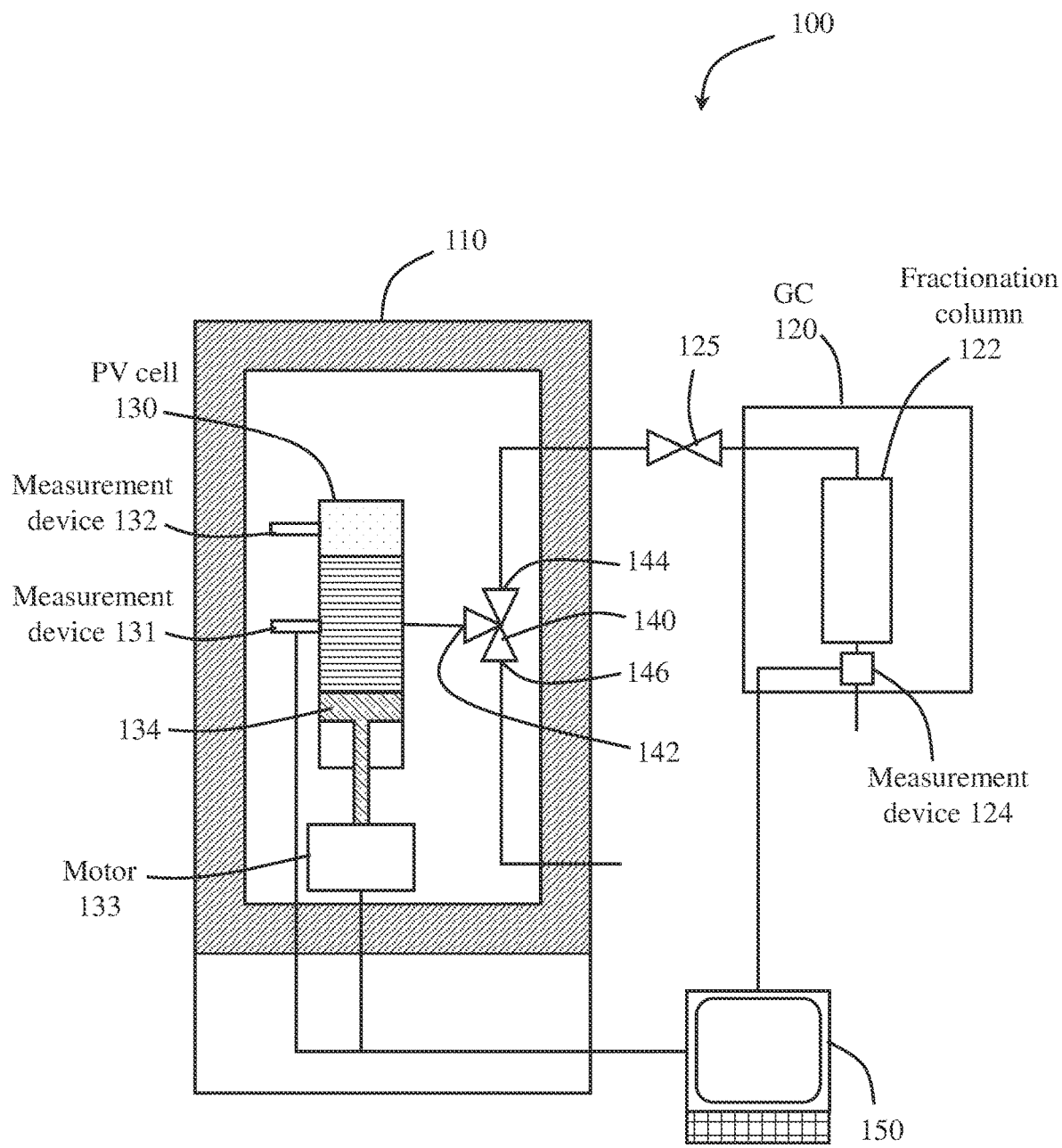
FIG. 2 shows a schematic view of another system according to embodiments of the present disclosure.

For example, FIG. 2 shows another example of a system 100 according to embodiments of the present disclosure including a PVT unit 110 and a connected GC 120. A PV cell 130 may be positioned within the PVT unit 110 and fluidly connected to an inlet 142 of a three-way valve 140 located inside the PVT unit 110. A plurality of PVT measurement devices 131, 132 may be provided in the PVT unit 110 (e.g., on the PV cell 130 and/or elsewhere within the interior of the PVT unit 110), which may measure, for example, pressure, temperature, etc.

A first outlet 144 of the three-way valve 140 may be fluidly connected to the GC 120, where one or more flow lines may extend from the first outlet 144 inside the PVT unit 110 to the GC 120 outside the PVT unit 110. The GC 120 may include at least one fractionation column 122, wherein the first outlet 144 is fluidly connected to the at least one fractionation column 122. A GC measurement device, e.g., detector 124, may be positioned at an outlet of the fractionation column 122 to detect the composition of the fluid exiting the fractionation column 122. A flow control valve 125 may be positioned along the flow line extending from a first outlet 144 of the three-way valve 140 to the GC 120, wherein the flow control valve 125 may be positioned outside of the PVT unit 110. The flow control valve 125 may be used to inject fluid into the GC 120 at a controlled rate.

A computing system (e.g., computer 150) may be in communication with the GC measurement device 124 and PVT unit measurement devices 131, 132. The computing system may, for example, collect and analyze data from the measurement devices 124, 131, 132. Further, the computing system may send command signals to one or more components within the system 100, which may include, for example, commands to run one or more test operations, open or close the three-way valve 140, control the injection rate into the GC 120, and/or to change a pressure or temperature setting. Data and/or command signals may be transmitted wirelessly or via wires.

For example, in some embodiments, a computing system may be used to send a command to open the three-way valve 140 and direct a portion of a fluid sample from within the PV cell 130 to the GC 120. In some embodiments, the three-way valve 140 may be fluidly connected to a first outlet to the fluid sample chamber of the PV cell 130, and a second valve may be fluidly connected to a second outlet to the fluid sample chamber of the PV cell 130, where the computing system may be used to operate the first and second valves to selectively direct fluid into and/or out of the PV cell 130 through the first and second outlets of the PV cell.

In some embodiments, the computing system may be in communication with a motor 133 (or pump or other power supply), which may be used to pressurize the PV cell 130 and/or the interior of the PVT unit 110. For example, in the embodiment shown, the computing system may send commands to a motor 133 positioned within the PVT unit 110 to control a piston 134 located in the PV cell 130. Movement of the piston 134 within the PV cell 130 may increase or decrease the pressure within the fluid sample chamber of the PV cell 130. As a fluid sample is subjected to different pressures in the PV cell 130, the fluid sample may undergo different phase changes, which may be analyzed during the PVT analysis.

PVT analysis may be conducted using a PVT unit, for example, to conduct one or more of an oil analysis for reservoir production, including, for example, recombined fluid analysis, capillary viscosity and density of the fluid, and solids detection, gas-condensate analysis (e.g., analysis of low and high gas oil ratios GOR), as well as chemical and solvent evaluation. PVT analysis may also include, for example, determining an oil formation volume factor (an oil volume at actual pressure, divided by volume of residual oil at standard conditions), a solution gas/oil ratio (the total standard volume of gas separated at lower pressure stages than the actual one, divided by the volume of the residual oil at standard conditions), oil density of the oil phase under the PV cell conditions, a gas formation volume factor (gas volume at the actual pressure divided by the volume of the same gas at standard conditions), a compressibility factor for the separated gas phase (a correction factor describing the deviation of a real gas from ideal gas behavior), gas gravity of the separated gas phase (molecular weight of the gas divided by the molecular weight of atmospheric air), and others.

Further, PVT analysis may include analysis of a fluid sample as it undergoes phase changes during pressure changes between pressures above the bubble point of the fluid sample and pressures below the bubble point of the fluid sample. The bubble point refers to the pressure conditions at which the first bubble of gas comes out of solution in oil under a given temperature. When a reservoir is under a pressure above the bubble point (an undersaturated reservoir) prior to beginning production, the pressure may decrease as fluid is produced from the reservoir to a pressure below the bubble point, in which case, a gas phase may begin to form in the reservoir.

To study how gas evolves from oil when the pressure falls below the bubble point, a PVT unit may utilize flash liberation, where the pressure is dropped suddenly, or differential liberation, where the pressure is gradually lowered. As the pressure in a PV cell containing a fluid sample is lowered and falls below the bubble point of the fluid sample, gas may separate from a liquid portion of the sample. The separated gas may be siphoned or drawn out of the PV cell, and the separate gas and liquid phases may be independently analyzed. In some embodiments, separated gas may be removed from the PV cell in stages, and the relative oil volumes remaining the in the PV cell may be measured after each stage of removal. After or during PVT analysis, at least a portion of a separated gas phase and/or liquid phase may be directly injected into a connected GC.

Gas chromatography may be conducted using the connected GC to analyze composition of a fluid mixture (e.g., a gas phase of a fluid sample from a PVT unit) by separating the mixture into parts. For example, a fluid mixture may be dissolved in a mobile phase fluid, and the mobile phase fluid may carry the fluid mixture through a fractionation column (or other structure) holding a stationary phase material. For example, the stationary phase material may line a fractionation column, and the mobile phase fluid may carry the fluid mixture along the stationary phase material through the fractionation column. The various constituents of the fluid mixture may travel through the fractionation column at different speeds, causing the different constituents to separate from the fluid mixture based on differential partitioning between the mobile and stationary phases. As different constituents are separated from the fluid mixture, one or more detectors may be used to detect the composition of the fluid mixture.

According to embodiments of the present disclosure, methods of analyzing fluid samples may include conducting a PVT analysis on a fluid sample from a well in a PVT unit as described herein (e.g., a PVT unit having a PV cell, which may contain the fluid sample, a three-way valve having an inlet fluidly connected to the fluid sample in the PV cell, and at least one measurement device), and transferring a portion of the fluid sample via the three-way valve to a GC located outside of the PVT unit to perform a gas chromatography analysis. Portions of the fluid sample in the PVT unit may be transferred to the GC during or after PVT analysis. For example, in some embodiments, portions of the fluid sample in the PVT unit may be directed to the connected GC at different stages during PVT analysis, which may be done to further analyze the fluid at different phases.

Figure 3:
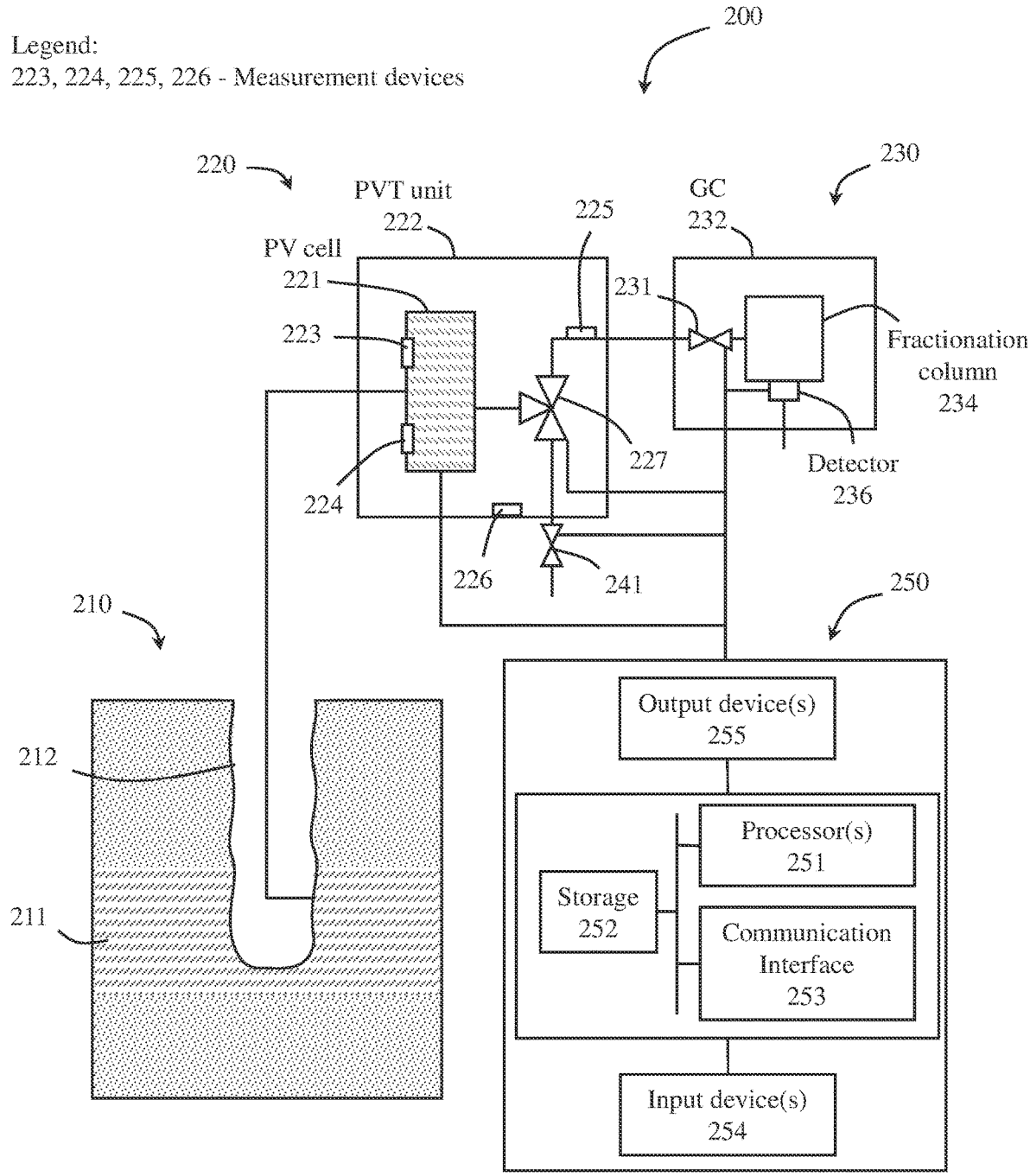
FIG. 3 shows a schematic view of another system according to embodiments of the present disclosure.

Examples of methods according to embodiments of the preset disclosure are described below with reference to FIG. 3, where FIG. 3 shows a schematic diagram 200 of systems according to embodiments of the present disclosure.

As shown in FIG. 3, methods of the present disclosure may include taking a fluid sample of a reservoir fluid from a reservoir 211 accessed by a well 212 (where the step of collecting a fluid sample is represented by system 210). The fluid sample may be collected at an early stage in the well's producing life, for example, from an exploratory well, to represent the reservoir under its initial conditions. Sample collection may be performed, for example, using downhole sampling, wellhead sampling, or surface recombination sampling processes and apparatuses.

For example, downhole sampling may include using a bottomhole sampler run downhole on a wireline to collect a reservoir fluid sample from a subsurface well stream under the bottomhole pressure. A bottomhole sampler may include a sample chamber and one or more fluidly connected valves that, when open, may collect a volume of the reservoir fluids to store in the sample chamber. When a reservoir is predicted to be initially at or below bubble point pressure, the sample may be collected with the well shut in. When a reservoir (e.g., reservoir 211) is predicted to be initially undersaturated (at a pressure above the bubble point pressure), the sample may be collected with the well (e.g., well 212) open (and may be producing at a rate low enough to keep the reservoir pressure above the bubble point pressure). Once a fluid sample is collected, the fluid sample may be brought to the surface and transferred to a PVT system (e.g., PVT system 220) as soon as possible.

In some embodiments, wellhead sampling may be used to collect a reservoir fluid sample, for example, when the reservoir fluid is an undersaturated oil. Such techniques may include collecting fluid from the wellhead (e.g., through a wellhead valve) and transferring the collected fluid directly to a PVT system (e.g., through tubing extending between the wellhead and the PVT system).

Once the fluid sample is collected from a downhole location, the fluid sample may be immediately transferred to a PVT system 220, where the fluid sample may be loaded into a fluid sample chamber within a PV cell 221 in a PVT unit 222. PVT analysis on the fluid sample may be conducted when the fluid sample has been transferred to the PV cell 221. Further, the temperature of the PV cell 221 may be kept at a constant temperature, e.g., a downhole or reservoir temperature from which the fluid sample was taken, during the PVT analysis. For example, the fluid sample may be collected from a location in a reservoir 211 under a reservoir pressure and a reservoir temperature (which may be measured, e.g., using downhole sensors), and then subjected to PVT analysis under the same reservoir temperature from which the fluid sample was collected.

PVT analysis may include charging the PV cell 221 to an initial pressure, which may be a pressure above the known or predicted bubble point pressure of the fluid sample. In some embodiments, the PV cell 221 may be charged to an initial pressure by pumping mercury into the sample-filled PV cell. As the mercury is pumped into the PV cell, the mercury compresses the fluid sample and the pressure within the PV cell increases. In some embodiments, a PV cell 221 may be charged by compressing the fluid sample (e.g., with a piston). Other means of pressurizing the PV cell 221 may be used to bring the fluid sample in the PV cell 221 to an initial pressure above the bubble point pressure.

After the PV cell 221 has been charged to an initial pressure, the pressure in the PV cell 221 may be reduced to a pressure below the bubble point pressure of the fluid sample, for example, by removing mercury from the PV cell. The pressure in the PV cell 221 may be reduced quickly in a flash liberation process or may be reduced slowly in a differential liberation process. The temperature of the PV cell 221 may be kept constant as the pressure changes within the PV cell 221.

As the pressure within the PV cell 221 is lowered below the bubble point pressure of the fluid sample, gas may begin to separate from the solution. Gas may continue to separate from the liquid portion of the fluid sample as the pressure continues to lower. Gas/liquid separation in the fluid sample may be conducted at different constant temperatures (e.g., which may correlate with different reservoir temperatures) in different PVT analysis processes, either using the same fluid sample or a different fluid sample collected from the same downhole location, to determine bubble point pressures of the fluid sample at the different temperatures.

The volume of liquid from the fluid sample in the PV cell 221 and the pressure within the PV cell 221 may be monitored as the pressure within the PV cell 221 is changed. For example, one or more measurement devices 223 in contact with the PV cell 221 may measure the volume of liquid from the fluid sample within the PV cell as the pressure is changed, and one or more measurement devices 224 (e.g., a pressure sensor) may be used to monitor the pressure within the PV cell 221 as mercury is pumped into and out of the PV cell 221. Further, one or more measurement devices 225, 226 (e.g., pressure and temperature sensors) may be positioned to measure conditions exterior to the PV cell 221 and within the PVT unit 222. For example, one or more temperature sensors 225 may be positioned along flow lines within the PVT unit 222 to measure the temperature in the PVT unit 222.

In some embodiments, the bubble point pressure of the fluid sample may be determined as pressure is reduced in the PV cell 221 by monitoring the pressure and volume of fluid within the PV cell 221 to determine a pressure volume relationship. Generally, the pressure volume relationship of the fluid sample in the PV cell 221 may be inverse, where there is a lower amount of liquid volume in the fluid sample in higher pressure conditions, and a larger liquid volume in lower pressure conditions. The pressure volume relationship may be plotted as a graph, where the slope of the pressure volume line may change at the bubble point pressure. Thus, in some embodiments, the bubble point pressure of a fluid sample may be determined by plotting the measured pressure and liquid volume in the PV cell 221 as pressure is reduced, where the bubble point pressure may be determined at a change in slope of the pressure v. volume line.

In some embodiments, other pressure, volume, temperature (PVT) tests that include changing the pressure, volume, and/or temperature of the fluid sample in the PV cell 221 may be conducted (e.g., a separation test). While conducting PVT tests, a gas phase may separate from a liquid phase in the fluid sample. Multiple different measurement devices or sensors (e.g., measurement devices 223, 224, 225, 226) may be used to measure and monitor conditions of the fluid sample and in the PV cell 221 as PVT tests are conducted. For example, a PVT analysis may include measuring at least one of oil density, gas density, solution gas oil ratio, bubble point pressure, formation volume factor, and viscosity. The results from the PVT analysis may be used, for example, for at least one of formation and reservoir evaluation, reservoir behavior forecasting, and planning enhanced oil recovery.

When a gas phase and a liquid phase of a fluid sample are separated in a PVT analysis, one or both of the gas and liquid may be removed from the PV cell for separate analysis. At least a portion of a gas phase and/or liquid phase of the fluid sample may be directed through an inlet to a three-way valve 227 located within the PVT unit 222 (and thus subjected to the same pressure and temperature conditions as the interior of the PVT unit 222), where the portion of the fluid sample may be directed through one or both of the two outlets of the three-way valve 227. For example, a first outlet of the three-way valve 227 may be fluidly connected to a GC system 230 and a second outlet of the three-way valve 227 may be fluidly connected to a gas compartment or other testing equipment. Additional valves 231, 241 (e.g., flow control valves or gate valves) may be positioned along flow lines from the first and second outlets of the three-way valve 227 to provide control over the discharge of the fluid from the PVT unit 222.

According to embodiments of the present disclosure, at least a portion of a gas phase and/or liquid phase of the fluid sample may be directed through the three-way valve 227 to an externally connected GC 232 after conducting a PVT analysis. A constant temperature may be maintained inside the PVT unit 222 during conducting the PVT analysis and when transferring the portion of the fluid sample to the GC 232.

After being directed out of the three-way valve 227, at least a portion of a fluid sample may be directed through a flow line fluidly connected to the GC 232, where it may be injected into the GC 232. In some embodiments, a flow control valve 231 or other fluid injection device may be used to inject the fluid sample into the GC 232 at a selected flow rate and/or under selected pressure conditions. When injected into the GC 232, one or more gas chromatography analyses may be conducted to determine one or more compositional parameters from the fluid sample. For example, a gas phase of a fluid sample may be injected into the GC 232, where components of the gas phase may be separated through one or more fractionation columns 234. One or more detectors 236 may be positioned at end of the fractionation column(s) 234 to detect separated compositional elements of the fluid sample.

According to embodiments of the present disclosure, one or more steps in methods disclosed herein may be controlled and/or automated using a computing system 250 in communication with the system 200. Further, one or more measurement devices 223, 224, 225, 226, 236 may send data signals to the computing system 250, where the data signals may be processed and interpreted. For example, a computing system 250 may send a command (wirelessly or wired) to a pressurizing system to change the pressure within the PV cell 221 to conduct one or more tests in a PVT analysis. One or more PVT unit measurement devices on the PV cell 221 may send, for example, fluid sample volume measurements or other sensing data indicating a phase change in the fluid sample to the computing system 250. After the computing system 250 receives and processes the PVT sensing data indicating a phase change in the fluid sample, the computing system 250 may send one or more commands to proceed with a subsequent step in analysis, including, for example, to alter the pressure in the PVT unit 222 and/or to open the three-way valve 227 to direct a portion of the fluid sample to through the three-way valve 227. For example, a first outlet of the three-way valve 227 may be opened to direct the fluid sample to an externally connected GC 232. In some embodiments, the computing system 250 may also send a command to control a flow control device 231 to inject a fluid sample at a selected flow rate or pressure into the GC 232. In some embodiments, one or more detectors 236 in the GC system 230 may be in communication with the computing system 250, where GC sensing data may be processed by the computing system 250.

A computing system 250 may include any combination of mobile, desktop, server, router, switch, embedded device, or other types of hardware. For example, the computing system 250 may include one or more computer processors 251, storage 252, including non-persistent storage (e.g., volatile memory, such as random access memory (RAM), cache memory) and persistent storage (e.g., a hard disk, an optical drive such as a compact disk (CD) drive or digital versatile disk (DVD) drive, a flash memory, etc.), a communication interface 253 (e.g., Bluetooth interface, infrared interface, network interface, optical interface, etc.), and numerous other elements and functionalities.

The computing system 250 may also include one or more input devices 254, such as a touchscreen, keyboard, mouse, microphone, touchpad, electronic pen, or any other type of input device, and one or more output devices 255, such as a screen (e.g., a liquid crystal display (LCD), a plasma display, touchscreen, cathode ray tube (CRT) monitor, projector, or other display device), a printer, external storage, or any other output device. One or more of the output devices may be the same or different from the input device(s). The input and output device(s) may be locally or remotely connected to the computer processor(s) 251 and storage 252. Many different types of computing systems exist, and the aforementioned input and output device(s) may take other forms.

The computer processor(s) 251 may be an integrated circuit for processing instructions. For example, the computer processor(s) may be one or more cores or micro-cores of a processor. In some embodiments, the computer processor(s) 251 may have function to execute instructions to perform PVT analysis operations (e.g., open/close valves, operate a pump at a selected speed, etc.) and/or perform gas chromatography operations.

The communication interface 253 may include an integrated circuit for connecting the computing system 250 to a network (not shown) (e.g., a local area network (LAN), a wide area network (WAN) such as the Internet, mobile network, or any other type of network) and/or to another device, such as another computing device. In some embodiments, the communication interface 253 may have the function to realize communication with the sensors, either via a wire or wirelessly, and with devices utilizing programmable logic controllers (PLCs).

Software instructions in the form of computer readable program code to perform embodiments of the disclosure may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that, when executed by a processor(s), is configured to perform one or more embodiments of the disclosure.

The extracted data may be used for further processing by the computing system. For example, the computing system 250, while performing one or more embodiments of the disclosure, may perform data comparison. The computing system 250 may also implement and/or be connected to a data repository. For example, one type of data repository is a database. In one or more embodiments, the data repository may be used to store retrieved sensing data and analysis results from PVT analysis and gas chromatography.

The computing system 250 may include functionality to present raw and/or processed data, such as results of comparisons, PVT analysis, gas chromatograph, and other processing. For example, data may be presented through a user interface provided by a computing device. The user interface may include a GUI that displays information on a display device, such as a computer monitor or a touchscreen on a handheld computer device. The GUI may include various GUI widgets that organize what data is shown as well as how data is presented to a user. Furthermore, the GUI may present data directly to the user, e.g., data presented as actual data values through text, or rendered by the computing device into a visual representation of the data, such as through visualizing a data model.

Figure 4:
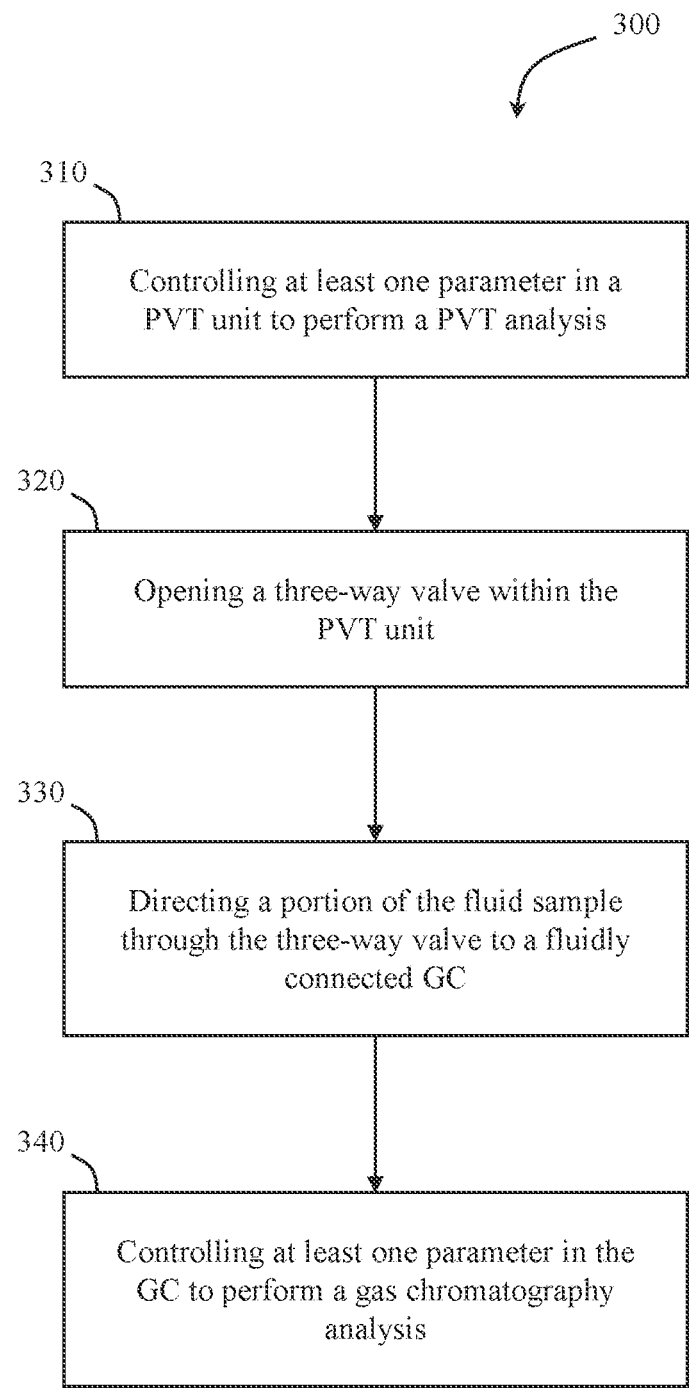
FIG. 4 shows a method according to embodiments of the present disclosure.

FIG. 4 shows an example of a method 300 for analyzing a fluid sample taken from a reservoir under a reservoir pressure and a reservoir temperature using a computing system. The method may include using a computing system to control at least one parameter in a PVT analysis of the fluid sample in a PVT unit (step 310), such as described herein. The computing system may be located outside of the PVT unit. The computing system may be used to control a PVT analysis, for example, by maintaining the reservoir temperature inside the PVT unit during the PVT analysis (e.g., by controlling a heating system within the PVT unit) and setting the pressure inside the PVT unit to be the same as the reservoir pressure for a period of time.

After completing at least one operation in a PVT analysis (e.g., determining a bubble point of the fluid sample), the computing system may be used to open a three-way valve within the PVT unit (step 320) and direct a portion of the fluid sample through the three-way valve (step 330). The computing system may also be used to maintain a selected temperature and pressure (e.g., the reservoir temperature and the reservoir pressure) within the PVT unit as the fluid sample is directed through the three-way valve.

The fluid sample may be directed from the three-way valve to a fluidly connected GC located outside of the PVT unit via one or more flow lines extending between an outlet of the three-way valve to the GC. Once a fluid sample is sent to the GC, the computing system may be used to control one or more parameters of a gas chromatography analysis (step 340).

Further, sensing data collected from the PVT analysis (e.g., PVT sensing data measured within the PVT unit during at least some of the PVT analysis) and/or the gas chromatography analysis (gas chromatography sensing data collected during at least some of the gas chromatography analysis) may be sent to the computing system for storage and/or for processing and further analysis. For example, sensing data collected from at least one of the PVT analysis and gas chromatography analysis may be used to characterize the fluid from the reservoir, which may be used in planning production from the reservoir.

In some embodiments, the computing system may be used to analyze the sensing data to determine when a next step in analysis is to occur. For example, PVT sensing data may be used to determine a volume of a liquid phase in the fluid sample, which may indicate when at least part of the fluid sample may be sent to the fluidly connected GC. When a preselected volume of a liquid phase in the fluid sample is determined, the computing system may be used to direct at least part of the liquid phase of the fluid sample through the three-way valve to the fluidly connected GC (or to an exit port in the PVT unit for discharge, storage, or a different analysis). As another example, PVT sensing data may be used to determine a volume of a gas phase in the fluid sample, which may indicate when at least part of the fluid sample may be sent to the fluidly connected GC. When a preselected volume of a gas phase in the fluid sample is determined, the computing system may be used to direct at least part of the gas phase of the fluid sample through the three-way valve to the fluidly connected GC.

Embodiments of the present disclosure may provide more accurate fluid analysis (including compositional analysis) of a fluid sample from a reservoir, which thereby may allow for more efficient and successful production from the reservoir. For example, conventional methods of PVT analysis and gas chromatography have included separating a fluid sample into a gas phase and a liquid phase and transferring the phases to different labs. Once the separate phases are injected into gas chromatographs to find the molar composition of each part, the molar composition may have changed (e.g., light components may escape and evaporate) during transfer, which may lead to inaccurate results. In contrast, systems and methods disclosed herein using a three-way valve positioned inside of a PVT unit may allow for direct fluid transfer (and thus more efficient transfer) between the PVT unit and a fluidly connected GC, thereby reducing the likelihood of lost light components in the fluid sample and improving the accuracy of the measured molar composition in the fluid sample.

Further, three-way valves used in PVT units disclosed herein may be designed to withstand PVT testing parameters, including high temperatures and high pressures mimicking the temperatures and pressures of the reservoir from which the tested fluid sample was collected.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims.

What is claimed:

1. A system, comprising:
a phase behavior analysis unit, comprising:
a housing;
a heating system connected to the housing and arranged to heat an interior of the housing;
a pressurizing system connected to the housing and arranged to pressurize the interior of the housing;
a pressure cell positioned in the interior of the housing; and
a three-way valve comprising one inlet fluidly connected to a chamber in the pressure cell via a fluid connection and two outlets,
wherein the three-way valve and the fluid connection between the chamber and the three-way valve are positioned in the interior of the housing;
a gas chromatograph that is fluidly coupled to the chamber in the pressure cell via the three-way valve; and
a computer system operatively connected to the heating system and the pressurizing system, the computer system comprising a processor and instructions for operating the phase behavior analysis unit, wherein the instructions comprise:
applying a temperature and a pressure in the chamber of the pressure cell, wherein the pressure ranges between 5,000 and 7,000 psi; and
maintaining the temperature and the pressure within the interior of the housing, such that the three-way valve and the fluid connection between the chamber and the three-way valve are under the temperature and the pressure of the chamber.

2. The system of claim 1, further comprising a second pressurizing system configured to pressurize the pressure cell, wherein the second pressurizing system comprises a pump located outside of the housing and fluidly connected to the pressure cell.

3. The system of claim 1, wherein the pressure cell is removable.

4. The system of claim 1, wherein the gas chromatograph comprises at least one fractionation column, and wherein one of the two outlets is fluidly connected to the at least one fractionation column.

5. The system of claim 1, wherein the computing system is in communication with at least one gas chromatograph measurement device and at least one phase behavior analysis unit measurement device.

6. The system of claim 1, further comprising a flow control valve positioned along a flow line extending from one of the two outlets of the three-way valve to the gas chromatograph, wherein the flow control valve is positioned outside of the phase behavior analysis unit.

7. The system of claim 6, further comprising a fluid compartment fluidly connected to a second outlet of the three-way valve, wherein the fluid compartment is positioned outside of the phase behavior analysis unit.

8. The system of claim 1, wherein the three-way valve is made of a nickel-molybdenum alloy.

9. A method, comprising:
transferring a fluid sample from a well directly into a pressure cell in a phase behavior analysis unit, the phase behavior analysis unit comprising:
the pressure cell comprising a chamber containing the fluid sample;
a three-way valve comprising an inlet fluidly connected to the chamber via a fluid connection; and
at least one measurement device, wherein the pressure cell, the three-way valve, the fluid connection, and the at least one measurement device are located inside a pressure-sealed housing of the phase behavior analysis unit
applying a pressure and a temperature to the fluid sample within the pressure cell to conduct a phase behavior analysis on the fluid sample;
transferring a portion of the fluid sample out of the pressure cell directly to the three-way valve;
maintaining the pressure and the temperature on the portion of the fluid sample as the portion of the fluid sample is directed from the pressure cell through the fluid connection and into the three-way valve; and
transferring the portion of the fluid sample from the three-way valve located inside the phase behavior analysis unit to a gas chromatograph located outside of the phase behavior analysis unit.

10. The method of claim 9, wherein the phase behavior analysis further comprises:
charging the pressure cell to an initial pressure; and
reducing pressure in the pressure cell to a pressure below a bubble point pressure of the fluid sample.

11. The method of claim 9, wherein the temperature in the pressure cell is held at a reservoir temperature and the pressure is held at a reservoir pressure ranging between 5,000 and 7,000 psi during the phase behavior analysis, wherein the reservoir temperature and the reservoir pressure are maintained on the portion of the fluid sample as the portion of the fluid sample is directed from the pressure cell into the three-way valve.

12. The method of claim 9, wherein the temperature is a constant temperature maintained inside the phase behavior analysis unit during conducting the phase behavior analysis and transferring to the gas chromatograph.

13. The method of claim 9, further comprising:
collecting the fluid sample from a downhole location using a downhole sampler;
bringing the fluid sample to a surface of the well; and
transferring the fluid sample to the phase behavior analysis unit as soon as the fluid sample is brought to the surface.

14. The method of claim 9, wherein the phase behavior analysis comprises measuring at least one of oil density, gas density, solution gas oil ratio, bubble point pressure, formation volume factor, and viscosity.

15. The method of claim 9, wherein a first outlet of the three-way valve is fluidly connected to the gas chromatograph and a second outlet of the three-way valve is fluidly connected to a gas compartment.

16. The method of claim 9, further comprising:
using a motor to apply the pressure to the fluid sample within the pressure cell, wherein the motor is located inside the housing of the phase behavior analysis unit; and
using a pressurizing system to apply the pressure inside the housing.

17. A method of analyzing a fluid sample taken from a reservoir under a reservoir pressure and a reservoir temperature, the method comprising:
using a computing system to control a phase behavior analysis of the fluid sample in a phase behavior analysis unit, the computing system located outside of the phase behavior analysis unit, wherein the controlling comprises:
maintaining the reservoir temperature inside the phase behavior analysis unit during the phase behavior analysis; and providing the reservoir pressure inside the phase behavior analysis unit;

using the computing system to open a three-way valve within the phase behavior analysis unit and direct a portion of the fluid sample directly from the phase behavior analysis unit to the three-way valve under the reservoir temperature and the reservoir pressure; and directing the portion of the fluid sample from the three-way valve to a gas chromatograph located outside of the phase behavior analysis unit.

18. The method of claim 17, further comprising sending sensing data to the computing system, wherein the sensing data is selected from phase behavior sensing data measured within the phase behavior analysis unit and gas chromatography sensing data from the gas chromatograph.

19. The method of claim 18, using the computing system to analyze the sensing data to determine a volume of a liquid phase in the fluid sample, wherein the portion of the fluid sample directed through the three-way valve comprises at least part of the liquid phase.

20. The method of claim 18, using the computing system to analyze the sensing data to determine a volume of a gas phase in the fluid sample, wherein the portion of the fluid sample directed through the three-way valve comprises at least part of the gas phase.

* * * * *